US00PP35943P2

(12) United States Plant Patent
Hansen

(10) Patent No.: US PP35,943 P2
(45) Date of Patent: Jul. 2, 2024

(54) ***HOSTA* PLANT NAMED 'ECHO THE SUN'**

(50) Latin Name: ***Hosta* hybrid (Tratt.)**
Varietal Denomination: Echo the Sun

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/300,986

(22) Filed: Jan. 13, 2022

(51) Int. Cl.
*A01H 5/02* (2018.01)
*A01H 6/12* (2018.01)

(52) U.S. Cl.
USPC ..... Plt./353
CPC ..... *A01H 6/12* (2018.05)

(58) Field of Classification Search
USPC ..... Plt./353
CPC ..... A01H 6/12; A01H 5/02
See application file for complete search history.

*Primary Examiner* — Keith O. Robinson

(57) ABSTRACT

A new and distinct *Hosta* plant named 'Echo the Sun' producing medium-sized low mounds of basal lanceolate leaves of yellowish to chartreuse color. The medium-sized leaves have a matte upper surface and glaucous underside. The flowers are white with light lavender centers and pale lavender backs. Flowers are attractively subtended by floral bracts making the whole scape more effective. 'Echo the Sun' is useful in the landscape, as a container plant, a specimen or en masse.

2 Drawing Sheets

Botanical classification: *Hosta* hybrid (Tratt.).
Variety denomination: 'Echo the Sun'.

STATEMENT REGARDING PRIOR DISCLOSURES UNDER 37 CFR 1.77(B)(6)

*Hosta* 'Echo the Sun' was first introduced by the inventor as a non-enabling description in registration of the name in early 2021 with the International Cultivar Registration Authority for the genus *Hosta*. Other non-enabling disclosure include the website introduction by Walters Gardens, Inc. on Dec. 1, 2021. No plants of *Hosta* 'Echo the Sun' have been sold in this country or anywhere in the world, nor has any enabling disclosure of the new plant been made.

BACKGROUND AND ORIGIN OF THE PLANT

The present invention relates to a new and distinct *Hosta* plant, *Hosta* 'Echo the Sun' hereinafter also referred to as the new plant or by the cultivar name, 'Echo the Sun'. *Hosta* 'Echo the Sun' was hybridized by the inventor on Aug. 5, 2014 at a wholesale perennial nursery in Zeeland, Mich., USA. The female parent was the proprietary unreleased hybrid known only by the breeder code 12-06-01 (not patented) and the male parent was a proprietary unreleased hybrid known only by the breeder code 11-304-2 (not patented). The seeds from this cross were planted in late fall of 2014 and a single seedling selection from this cross eventually produced the new plant. The new plant was assigned the breeder code 14-408-3 and passed the initial evaluation in the summer of 2015. 'Echo the Sun' has been asexually propagated by division at the same nursery since 2018 and also by careful shoot tip plant tissue culture with the resultant asexually propagated plants having retained all the same traits as the original plant. *Hosta* 'Echo the Sun' has been stable and reproduced true to type plants in successive generations of asexual reproduction.

There are nearly 7,000 registered and established *Hosta* cultivars with The American *Hosta* Society, which is the International Cultivar Registration Authority for the genus *Hosta*. Several of these have blue-green leaf blades. The most similar *Hosta* cultivars known to the applicant are: 'Neptune' U.S. Plant Pat. No. 19,674, 'Party Streamers' U.S. Plant Pat. No. 33,277, Dancing Queen' (not patented), 'River of Gold' (not patented) and 'Seasons in the Sun' [copending] U.S. Plant patent application Ser. No. 17/300,988.

The female parent (12-06-01) is larger in habit and in foliage size, and the leaves are not as sinuate on the margin and the yellow color becomes more chartreuse in the summer. The proprietary unnamed male parent (11-304-2) is larger in habit and foliage.

'Neptune' has a bluish foliage and longer petioles. 'Party Streamers' is more compact and shorter in habit, has a narrower leaf blades and petioles. 'Dancing Queen' has larger and more arching foliage with less sinuate margins, less folding and the yellow spring color becomes more chartreuse in the summer. 'River of Gold' has a larger habit and larger leaves that are less sinuate and the leaf color is more chartreuse and less in the yellowish hue. 'Seasons in the Sun' has a larger habit and larger leaves that are more rounded with a less sharply acute apex.

Other *Hosta* cultivars may have individual traits similar to 'Echo the Sun' but the new plant differs from the above listed cultivars and all other *Hostas* known to the applicant, by the combination of the following traits.

1. Leaves are medium-sized, lanceolate, with narrowly acute apices and cordate bases;
2. Leaves are slightly folded with nicely rippled margins;
3. Leaves are yellowish to chartreuse with the top surface matte and bottom surface glaucous;
4. and petioles produce a tight, medium-sized, mounded habit;

5. Flowers are white, with light lavender central lines and pale lavender backs;
6. Flowers are densely arranged on scapes with the first flowers beginning to open above the foliage;
7. Floral bracts of light yellowish-green with a blush of lavender subtend each flower;
8. The habit is a medium-sized low mound.

BRIEF DESCRIPTION OF THE DRAWING

The photograph of the new plant demonstrates the overall appearance of the new plant, including the unique traits. The colors are as accurate as reasonably possible with color reproductions. Ambient light spectrum, temperature, source and direction may cause the appearance of minor variation in color.

The drawings show a six-year-old 'Echo the Sun' plant in a trial garden at a nursery in Zeeland, Mich. with supplement fertilizer and water as needed.

DETAILED BOTANICAL DESCRIPTION

Figure 1:
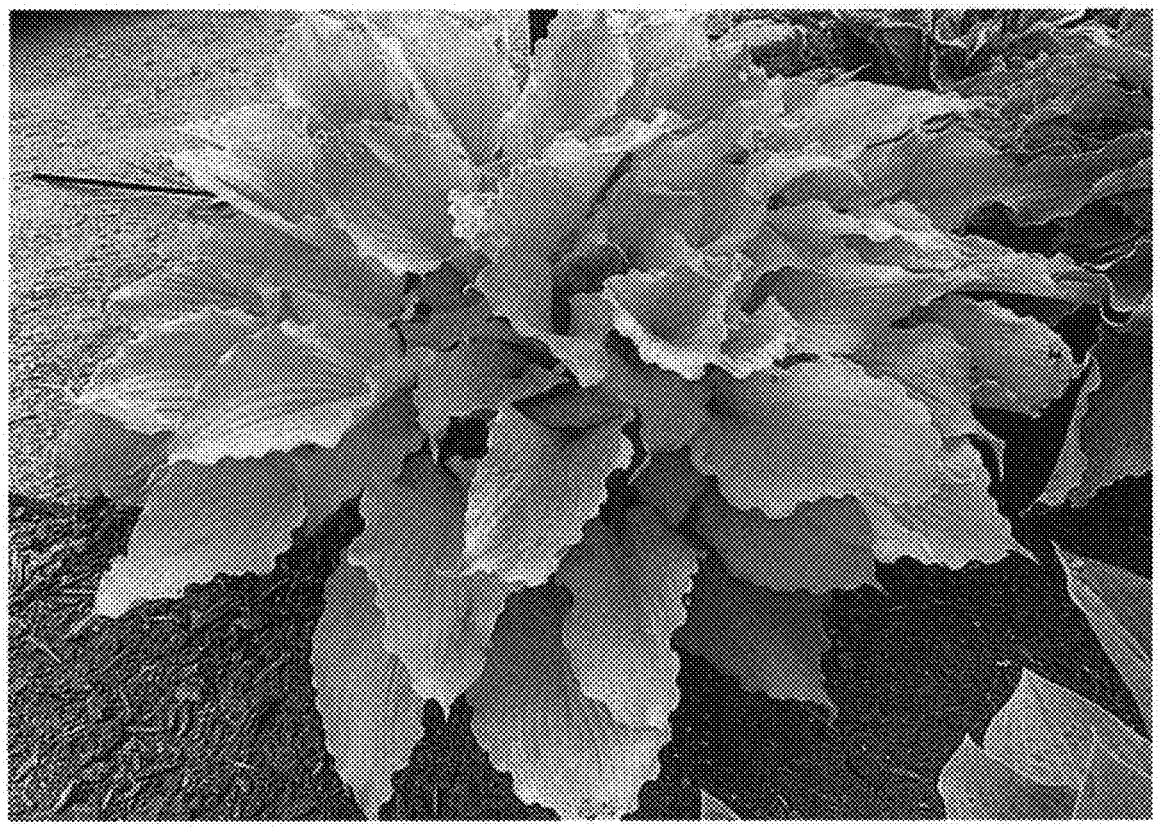
FIG. 1 shows the landscape foliage habit of a new plant prior to flowering.
Figure 2:
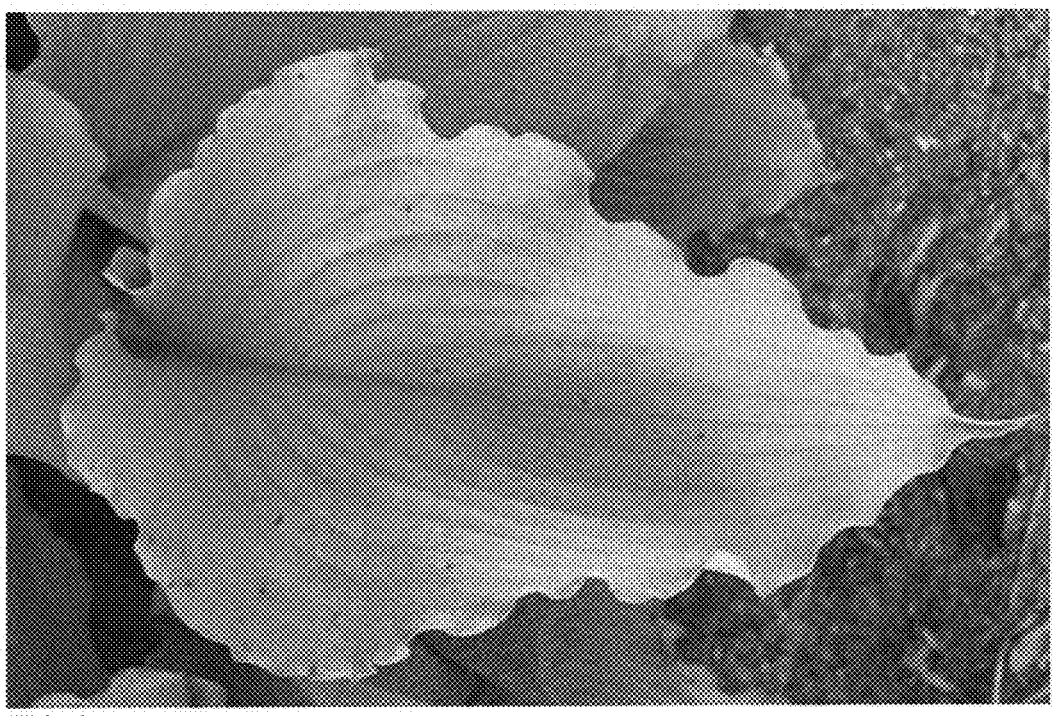
FIG. 2 shows a close-up of a leaf.
Figure 3:
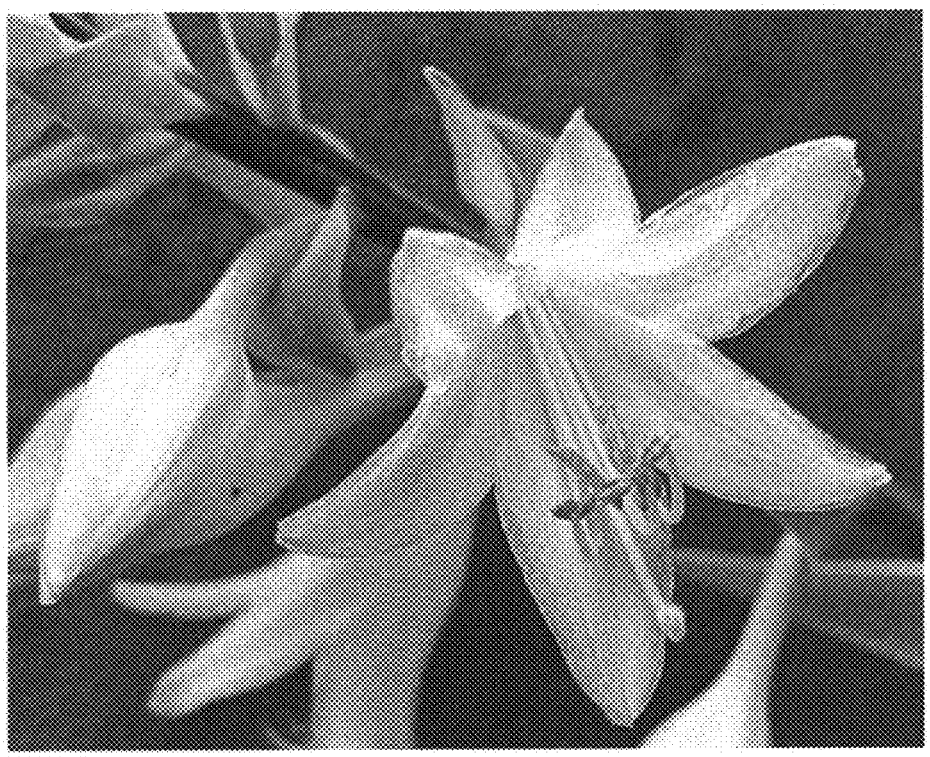
FIG. 3 shows a close-up of the flower, buds and foliar bracts.

The following descriptions and color references are based on the 2015 edition of The Royal Horticultural Society Colour Chart except where common dictionary terms are used. The new plant, *Hosta* 'Echo the Sun', has not been observed under all possible environments. Those skilled in the art will appreciate that certain characteristics will vary with plants that are more mature or plants that are less mature. The phenotype may vary slightly with different environmental conditions, such as temperature, light, fertility, moisture and maturity levels, but without any change in the genotype. The following observations and size descriptions are of a six-year-old plant in a shaded trial garden in Zeeland, Mich. with supplemental water and fertilizer.

Botanical classification: *Hosta* x hybrid;

Parentage: Female or seed parent is 12-06-01; male or pollen parent is 11-304-2;

Propagation: Garden division and sterile shoot tip tissue culture;

Time to initiate roots from tissue culture: About two to three weeks;

Growth rate: Moderately vigorous;

Crop time: About three months to four months to finish during the spring in a one-liter container from rooted tissue culture plantlet during the warm portion of the growing season;

Rooting habit: Fleshy, lightly branching;

Root color: Nearest RHS NN155C when actively growing;

Plant shape and habit: Hardy herbaceous perennial with basal rosette of leaves emerging from rhizomes producing a medium-sized mound of outwardly extending petioles and leaves and arching scapes flowering above foliage;

Plant size: Foliage height to about 48.5 cm above soil line to the top of the leaves, to about 68.5 cm tall to the top of the flowers and to about 112.0 cm wide at the widest point just above the soil line;

Foliage description: Lanceolate; narrowly acute apex, cordate base; margin entire, and sinuate; slightly folded along midrib; glabrous both surfaces, smooth, and adaxial matte and abaxial highly glaucous; flexible but stiff;

Leaf blade size: To about 21.6 cm long and about 14.0 cm wide about one-third way from the base; average about 19.5 cm long and 13.0 cm wide; not variegated;

Leaf blade color: Early season and expanding adaxial between RHS 145B and RHS 145C, abaxial between RHS 145B and RHS 145C; mid-season and mature adaxial variable, between RHS 11C and between RHS 146D and RHS N144D, abaxial variable, nearest RHS 160D, RHS 160C, RHS 145A and between RHS 145A and RHS 146D;

Veins: 12 to 13 pairs plus midrib; slightly impressed adaxial and costate and smooth abaxial;

Vein color: Young adaxial nearest RHS 145C, abaxial between RHS 145A and RHS 146D; mature adaxial variable, nearest RHS 146D and between RHS 146C and RHS 145A, abaxial between RHS N144D and RHS 145A;

Petiole: Glabrous and moderately glaucous both adaxial and abaxial; moderately concavo-convex; stiff; to 27.0 cm long and 22.0 mm wide at base and about 4.0 mm deep, average about 25.5 cm long and 20.0 mm wide and 3.5 mm deep;

Petiole color: Young adaxial between RHS 147D and RHS 145C distally becoming increasingly maculate with nearest RHS N186C, young abaxial 147D and RHS 145C distally becoming increasingly maculate with nearest RHS N186C, mature adaxial between RHS 146C and RHS 145A, abaxial midrib between RHS 146C and RHS 145A, both adaxial and abaxial becoming increasingly maculate in distal 5.0 cm with nearest RHS N187C;

Flower description:

Buds one to two days prior to opening: Clavate with acute apex and narrow tube and rounded base; about 38.0 mm long and 11.0 mm in diameter at the widest portion in the bulb, tube to about 14.0 mm long and to about 3.0 mm diameter;

Bud color: Nearest RHS NN155C lightly blushed with nearest RHS 85C to apical 10.0 mm and basal 10.0 mm;

Flowers: Perfect; incomplete; flared campanulate; attitude outwardly; to 57.0 mm long to exserted pistil; corolla to 47.0 mm long and 27.0 mm wide at apex, fused in basal 27.0 mm, free in the distal 21.0 mm, decreasing distally; corolla tube portion 16.0 mm long and 3.0 mm diameter; with rounded base; flowers tightly arranged on scape;

Flowering lasting: Persists for a normal period, usually about one day on plant;

Flowering period: Scapes remain effective with flowers beginning mid-July for about three and a half weeks; with about 40 flowers per scape; mostly secund;

Fragrance: No detectable fragrance;

Tepal: Two sets of three; clavate; entire margins; acute apex; fused in basal 27.0 mm; glabrous adaxial and abaxial; outer set to about 9.0 mm wide and 48.0 mm long; inner set to about 11.0 mm wide and 48.0 mm long;

Tepal color: Outer set adaxial nearest RHS 85D in 3.0 mm longitudinal center and nearest RHS NN155D along edges, abaxial with faint blush of nearest RHS 85D along center and nearest RHS NN155D along edge; inner set adaxial nearest RHS 85D in 3.0 mm longitudinal center and nearest RHS NN155D along edges, abaxial with faint blush of nearest RHS 85D along center and nearest RHS NN155D along edge, with a transparent 0.5 mm wide margin;

Gynoecium: Single; to about 65.0 mm long; superior;

*Style*.—cylindrical; glabrous; to about 58.0 mm long and 0.7 mm diameter; straight with distal 7 mm arcuate upwards 90°; color nearest RHS 145D proximally and nearest RHS 155D distally.

*Stigma*.—puberulent; globose; about 1.0 mm long and 1.0 mm diameter; color nearest RHS 155B.

*Ovary*.—Ellipsoidal; superior; apex rounded; base rounded to truncate; sides lightly furrowed, about 6.0 mm long and 2.5 mm diameter; color nearest RHS 145A.

Androecium: Six;

*Filaments*.—Six; cylindrical; approximately 54.0 mm long and 0.5 mm in diameter; curved or bent upwardly about 90° in the distal 7.0 mm; color in distal one-half nearest RHS 155D transitioning to nearest RHS 145D in the proximal one-third.

*Anthers*.—Ellipsoidal with rounded ends; basifixed, longitudinally dehiscent; about 5.0 mm long and 2.0 mm wide when fully developed; color variable, nearest RHS 199B and RHS 163D.

*Pollen*.—Abundant; spherical; less than 0.1 mm long; color nearest RHS 14A.

Peduncle: Cylindrical; usually one per mature division; about 8 per plant; glabrous; moderately glaucous; arching; to about 68.5 cm tall, and about 9.0 mm in diameter at base, average about 57.0 cm tall and 8.0 mm diameter at base;

Inflorescence: Flowering portion about 25.0 cm long and 8.0 cm wide; with bracts of light yellowish-green with lavender blushing subtending each flower;

Peduncle color: Proximal portion below leaves nearest RHS 146C and distal portion nearest RHS 146D;

Pedicel: Cylindrical; glabrous; slightly lustrous; to about 14.0 mm long and 1.5 mm diameter, decreasing distally; attitude arcuate outwardly;

Pedicel color: Between RHS N144A and RHS 146D;

Floral bracts: Each flower normally subtended by a single bract; lanceolate; narrowly acute apex and truncate base; entire margin; glabrous and slightly glaucous abaxial and adaxial; to about 28.0 mm long 10.0 mm wide, decreasing distally;

Bract color: At flowering adaxial and abaxial nearest RHS 191D with variable blush of nearest RHS 85D, becoming nearest RHS 160C adaxial and between RHS 146D and RHS 160B abaxial;

Fruit: Non-fleshy, dehiscent, tri-loculicidal capsule; oblong ellipsoidal; rounded base; apiculate apex; about 2.0 cm long and 5.0 mm in diameter; color as maturing nearest RHS 146D, when nearly mature and prior to dehiscence nearest RHS 150D and upon dehiscence nearest RHS 161C;

Seeds: Elliptic; with flattened wing surrounding embryo positioned toward one end of ellipse; about 7 mm long, 2.5 mm wide and 1.0 mm thick at embryo; typically 10 to 30 per capsule; color nearest RHS 202A with maturity;

Disease resistance: The thick glaucous leaves provide some resistance to slug feeding. Other resistance to pests (including: *Odocoileus virginianus* and *Oryctotagus cuniculus*) and diseases common to *Hostas* is equal that typical of other cultivars.

Growth: The plant grows best and shows best coloration with plenty of moisture, adequate drainage and light shade, but is able to tolerate some drought when mature.

Hardiness: At least from USDA zone 3 through 8, and other disease resistance is typical of that of other *Hostas*.

It is claimed:

1. A new and distinct *Hosta* plant named *Hosta* 'Echo the Sun' as herein described and illustrated.

* * * * *